United States Patent [19]

Kikuchi

[11] Patent Number: 4,823,370
[45] Date of Patent: Apr. 18, 1989

[54] X-RAY DIAGNOSTIC APPARATUS

[75] Inventor: Katsuya Kikuchi, Tochigi, Japan

[73] Assignee: Kabushiki Kaisha Toshiba, Kawasaki, Japan

[21] Appl. No.: 106,956

[22] Filed: Oct. 13, 1987

Related U.S. Application Data

[63] Continuation of Ser. No. 601,349, Apr. 17, 1984.

[30] Foreign Application Priority Data

Apr. 25, 1983 [JP] Japan ................................. 58-73552
May 11, 1983 [JP] Japan ................................. 58-80971

[51] Int. Cl.$^4$ ............................................. H05G 1/64
[52] U.S. Cl. ............................................ 378/99; 378/7
[58] Field of Search ................... 378/2, 7, 87, 99, 204, 378/207, 154, 155, 149; 358/111, 161; 364/414

[56] References Cited

U.S. PATENT DOCUMENTS

| | | |
|---|---|---|
| 2,336,026 | 12/1943 | Millenaar . |
| 2,679,008 | 5/1953 | Hall . |
| 3,860,821 | 1/1975 | Barrett . |
| 4,087,837 | 5/1978 | Geluk .................... 378/99 |
| 4,114,041 | 9/1978 | Oliver ..................... 378/7 |
| 4,286,156 | 5/1979 | Wagner .................. 378/7 |
| 4,380,817 | 4/1983 | Harding et al. . |
| 4,380,818 | 4/1983 | Pfeiler . |
| 4,399,547 | 8/1983 | Riederer et al. . |
| 4,549,307 | 10/1985 | Macovski ............... 378/7 |
| 4,550,419 | 10/1985 | Aichinger et al. . |
| 4,599,742 | 7/1986 | Kikuchi et al. . |
| 4,656,650 | 4/1987 | Kikuchi et al. . |

FOREIGN PATENT DOCUMENTS

| | | |
|---|---|---|
| 0001523 | 4/1979 | European Pat. Off. . |
| 0105618 | 4/1984 | European Pat. Off. . |
| 0123276 | 10/1984 | European Pat. Off. . |
| 2454537 | 5/1976 | Fed. Rep. of Germany . |
| 2452166 | 5/1976 | Fed. Rep. of Germany ...... 378/154 |
| 2459890 | 7/1976 | Fed. Rep. of Germany ...... 358/111 |
| 3304213A1 | 8/1984 | Fed. Rep. of Germany . |
| 2526575 | 11/1983 | France . |

OTHER PUBLICATIONS

Ser. No. 016,129, 02/18/87.
Ser. No. 673,792, 11/21/84.
Ser. No. 792,855, 10/30/85.
Ser. No. 857,050, 04/29/86.

Primary Examiner—Craig E. Church
Attorney, Agent, or Firm—Finnegan, Henderson, Farabow, Garrett, & Dunner

[57] ABSTRACT

An X-ray generator projects X-rays into an object under examination. An X-ray detector detects the X-ray image data transmitted through the object. The transmitted X-ray image data is digitized by an A/D converter and visually displayed by a monitor. For effecting such display, an X-ray shield member having an X-ray shield section configured in a predetermined pattern is set in an X-ray projection area. The transmitted X-ray image data containing the X-ray shield section data obtained under this condition is supplied to a scattered X-ray intensity computing circuit through first and second switching circuits and a memory. The computing circuit computes the scattered X-ray component. Then, the X-ray shield member is retracted from the X-ray projection area. Under this condition, the transmitted X-ray image data is supplied through the first and second switching circuits to a subtracting circuit. The substracting circuit subtracts the scattered X-ray component previously obtained from the transmitted X-ray image data, thereby to send only the primary X-ray component to the monitor.

7 Claims, 9 Drawing Sheets

F I G. 6(A) 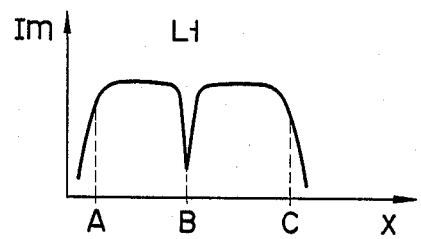
F I G. 6(B) 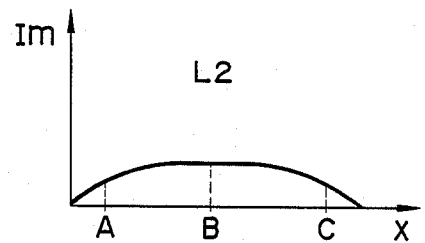
F I G. 6(C) 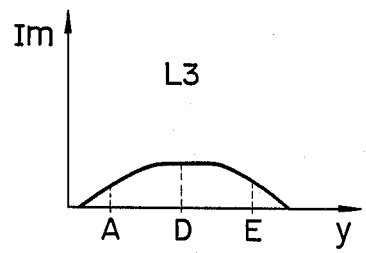

FIG. 7
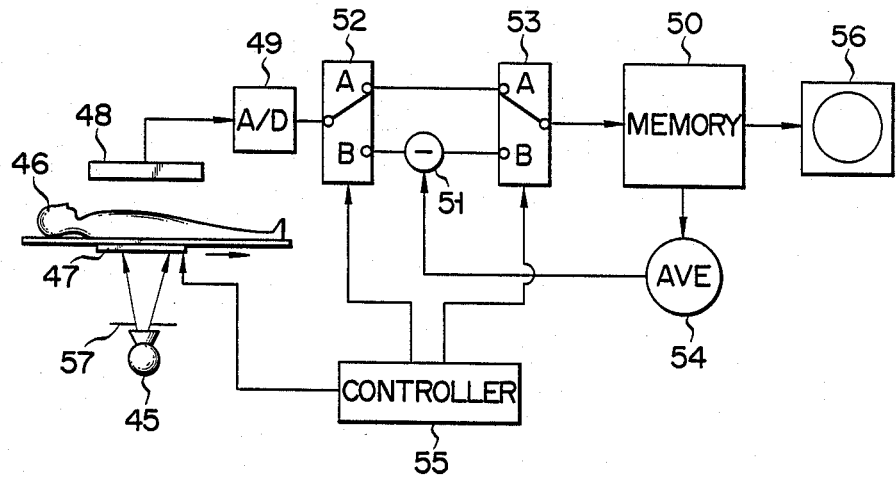
FIG. 8
FIG. 9
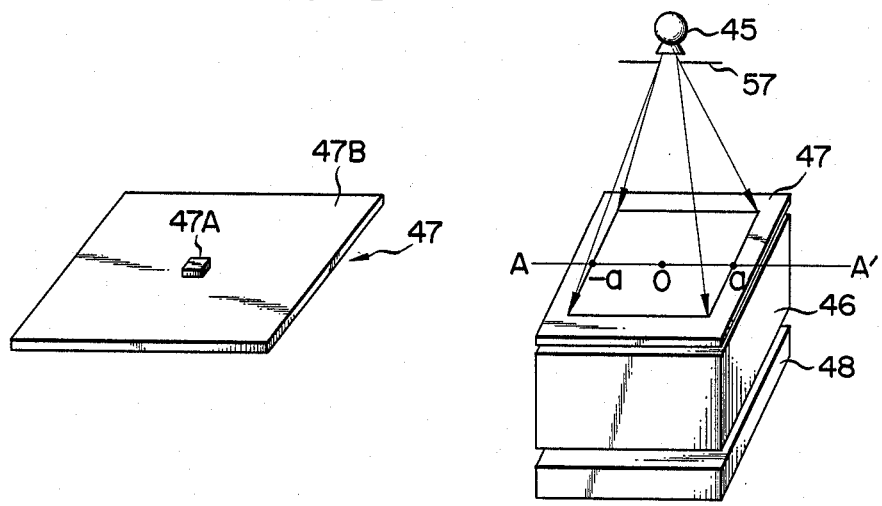

F I G. 10
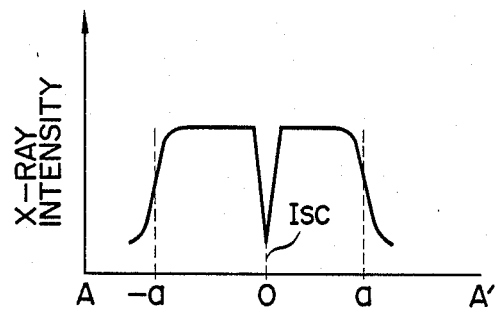
F I G. 11
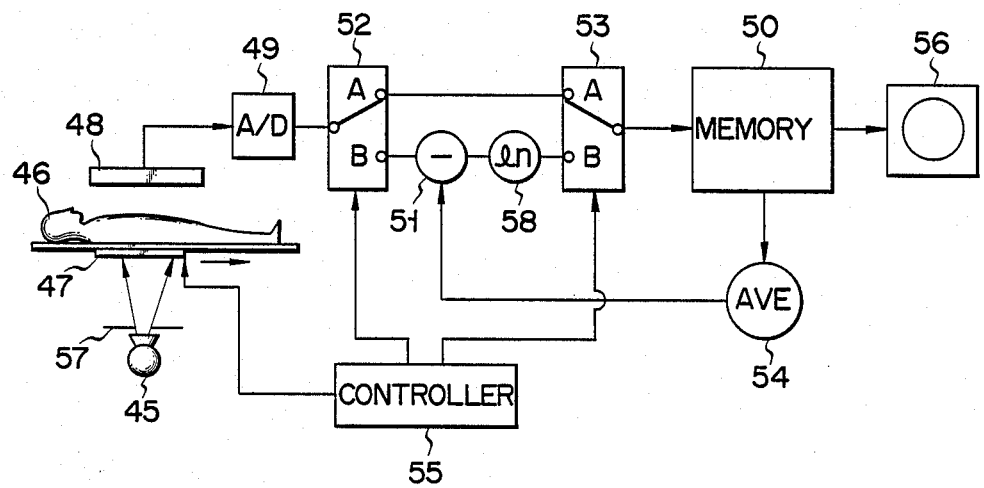

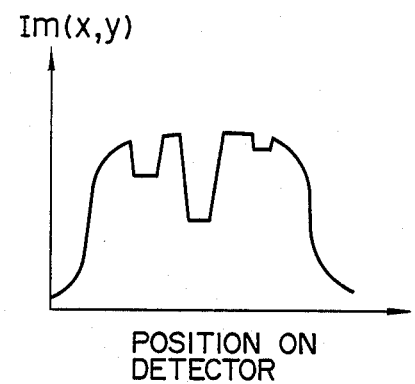
F I G. 16(A)
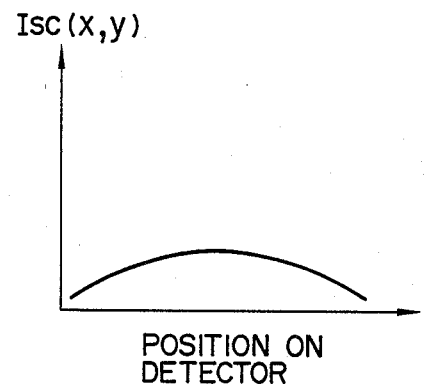
F I G. 16(B)
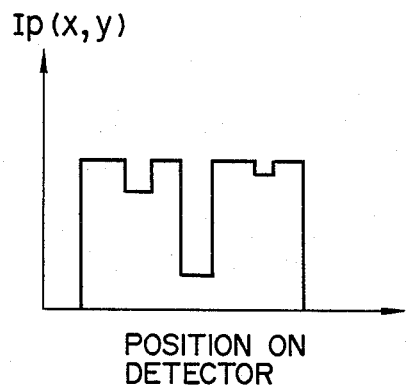
F I G. 16(C)

X-RAY DIAGNOSTIC APPARATUS

This application is a continuation of application Ser. No. 601,349, filed Apr. 17, 1984.

BACKGROUND OF THE INVENTION

This invention relates to an X-ray diagnostic apparatus in which a transmitted X-ray image of an object to be examined, e.g., a patient, is available for diagnostic purposes, and more particularly to an X-ray diagnostic apparatus by which a transmitted X-ray image of the object is obtained, based only upon primary X-rays, without any adverse influences caused by the scattered X-ray as well as the systems structural factors.

Generally, in the X-ray diagnostic apparatus set forth in the preamble, X-rays incident on an X-ray detector contain not only primary X-rays but also X-rays which are scattered by the object under examination. The scattered X-rays constitute one of the major causes of deteriorated contrast and resolution in the transmitted X-ray image. This makes it necessary to eliminate an image component on the scattered X-rays from the transmitted X-ray image data as sensed and provided by the detector.

One of the approaches to eliminate the scattered X-ray component is to use a so-called "Buckey Blend" or an elimination grid for the scattered X-rays (referred to as a "grid"). This approach also involves a problem in that there is a limit in the scattered X-ray elimination because the grid per se scatters the X-rays incident thereupon.

The elimination of the scattered X-rays is very significant in the field of X-ray diagnosis for the reasons that it improves an image quality, such as contrast and resolution, and thus allows a logarithm conversion of primary X-rays image data, thereby obtaining an accurate attenuation quantity of X-rays caused when the X-rays pass through the object. Many studies have been made on the scattered X-rays, aiming at their effective elimination. The complicated phenomena of the scattered X-rays impede or almost reject a theoretical approach to this problem. This is the present stage of technology in this field.

SUMMARY OF THE INVENTION

For the above background reasons, an object of the present invention is to provide, by introducing a novel technical idea, an X-ray diagnostic apparatus which can effectively eliminate the scattered X-ray image component from the transmitted X-ray image components as obtained by the X-ray detector.

In an X-ray diagnostic apparatus according to the present invention, an X-ray shield means having an X-ray shield section configured in a predetermined pattern may be placed in and retracted from an X-ray projection area in visually displaying the digital image data of X-rays output by an X-ray detector, the data being transmitted through an object as the result of X-ray irradiation of the object under diagnosis. A means computes the scattered X-ray component using the X-ray transmission data containing the image data collected from the X-ray shield section when the X-ray shield means is placed in the X-ray projection area. A compensating means subtracts the scattered X-ray component, computed and produced by the scattered X-ray computing means, from the X-ray transmission data, produced on the condition that the X-ray shield means is not placed in the X-ray projection area, thereby to produce only the primary X-ray component.

With such an arrangement, the scattered X-ray component may effectively be removed from the transmitted X-ray data. Therefore, the displayed image is based only on the primary X-ray component. A high quality image is produced which is free from blur and improved in contrast and sharpness. Such a high quality image enables a doctor, for example, to perform effective diagnosis.

BRIEF DESCRIPTION OF THE DRAWINGS

This and other objects and features of the present invention may be best understood by reference to the specification and the accompanying drawings, in which:

FIG. 6(A) graphically illustrates the intensity distribution of X-rays along a line L1 shown on the X-ray detector of FIG. 5;

FIG. 6(B) graphically illustrates the intensity distribution of X-rays along a line L2 shown on the X-ray detector of FIG. 5;

FIG. 6(C) graphically illustrates the distribution of incident X-rays along a line L3 shown on the detector in FIG. 5;

FIG. 7 is a schematic diagram illustrating a first embodiment of an X-ray diagnostic apparatus according to the present invention;

FIG. 8 is a perspective view of an X-ray shield plate used in the embodiment of FIG. 7;

FIG. 9 is a diagram illustrating irradiation of X-rays with the X-ray shield plate set in the X-ray irradiation field;

FIG. 10 is a graph showing the intensity distribution of X-rays detected by the X-ray detector, installed as shown in FIG. 9;

FIG. 11 is a schematic diagram showing a modification of the embodiment shown in FIG. 7;

FIG. 16(A) is a plot of intensity distribution of X-rays incident on the X-ray detector as plotted when the contrast phantom is radiographed; and FIG. 16(B) is a plot of the intensity distribution curve of the scattered X-rays component of the X-rays incident on the detector when the contrast phantom is radiographed; and FIG. 16(C) is a plot of intensity distribution of X-rays after the application of a compensating process.

DETAILED DESCRIPTION OF THE PREFERRED EMBODIMENTS

Before proceeding with the description of the various preferred embodiments of the present invention, the principle of the present invention will be described in detail.

In the present invention, X-rays are projected through the object to be examined under the condition that an X-ray shield member with a predetermined pattern is placed in the X-ray projection area. In such a condition, the transmitted X-ray image data detected by the detector in the area of the X-ray shield member contains only the scattered X-rays because the primary X-rays are shielded by the X-ray shield member. The present invention is based on the above assumption.

To embody the above idea, the scattered X-ray component is calculated using the X-ray transmission image data obtained in the above way.

Then, an object is irradiated with X-rays based on the condition that the X-ray shield member is not placed in the X-ray projection area. Under this condition, the X-ray transmission image data containing both the primary X-rays and the scattered X-rays is detected by the X-ray detector. The scattered X-rays as already calculated are substracted from the transmitted X-ray image data. As a result, detection data based on only the primary X-ray component are derived.

The above principle leads to the first and second application principles as given hereinafter.

It is assumed that X-rays incident on an object under examination are generally classified into "primary X-rays" which directly transmit through the object and enter into the X-ray detector, and "scattered X-ray" which are absorbed or scattered by the object through interactions of the X-rays with atoms constituting the object. In the energy range of medical X-rays (radiated under 50 KVp to 120 KVp of the X-ray tube voltage), some causes of X-ray scattering are known, for example, photoelectric effects, Compton effects, Thomson effects, and the like. These phenomena cooperate to cause the scattered X-rays to have adverse effects on the transmitted X-ray image to be described later. In general, because the scattered X-rays incident on the X-ray detector experience multi-scattering within the object, it is very difficult to exactly grasp an intensity and a spatial spread of an incident X-ray beam. This phenomenon is explained as follows.

Figure 1:
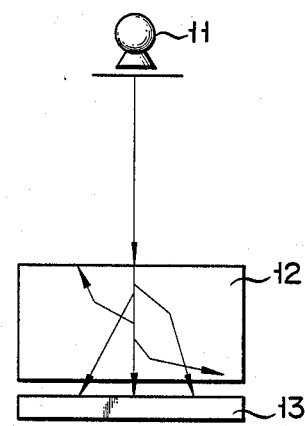
FIG. 1 is an illustration for explaining the occurrence of scattered X-rays when an X-ray is projected toward an object under examination.
Figure 2:
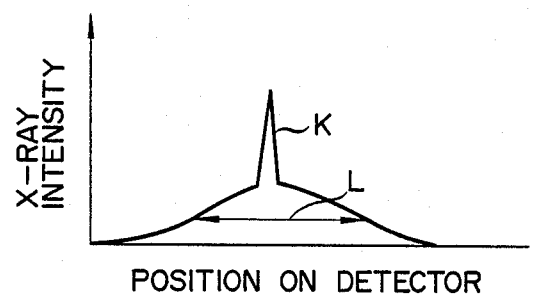
FIG. 2 shows a graphic representing X-ray intensity vs. detection position on an X-ray detector.

FIG. 1 schematically illustrates how an X-ray radiated from an X-ray source 11, such as an X-ray tube, is scattered within an object 12 under examination and reaches an X-ray detector 13, while depicting a spatial spread with respect to detecting positions of the X-ray detector. FIG. 2 illustrates the X-ray intensity distribution over the detecting positions of the X-ray detector 13. As seen from FIG. 2, a narrow spread, or spatial distribution of a sharp peak (as indicated by character K), located substantially at the center of the distribution curve, is caused by an inherent matter of the diagnosis system, for example, an X-ray focal spot and a wide spread (as indicated by character L) is caused by the scattered X-rays.

In accordance with the study on the scattered X-rays by the inventors of the present patent application, the following recognition is made: in the medical X-ray energy range, the intensity distribution of scattered X-rays emanated from an object with a thickness substantially equal to that of a human body is generally expressed by the following equation;

$$Isc(x, y) = A \int_{-a}^{a} \int_{-b}^{b} f(Ip(x', y'))g(x - x', y - y')dy'dx' \quad (1)$$

where Isc(x, y) indicates the intensity distribution of the scattered X-rays over detecting positions of the detector. The character A designates a constant in the above equation (1). The integration intervals $-a$ to a and $-b$ to b in the above equation define an area projected by the X-rays (referred to as an "X-ray projection area" hereafter) on the detecting positions of the detector. More exactly, $-a \leq x \leq a$ and $-b \leq y \leq b$. In the above equation, $f(Ip(x,y))$ is a function of the primary X-ray intensity distribution $Ip(x, y)$, and $g(x,y)$ is a function defining the spatial spread of the scattered X-rays with respect to the incident X-rays as a pencil beam, and is a so-called "impulse response function".

It is readily understood from the above description that this "impulse response function" means a function for defining the spatial spread of the scattered X-rays with respect to the incident X-rays as a fan-shaped beam or a parallel beam. The function $g(x, y)$ satisfies the following equation (2)

$$\int_{-\infty}^{\infty} \int_{-\infty}^{\infty} g(x, y)dxdy = 1 \quad (2)$$

Generally, A, $f(Ip(x, y))$, and $g(x, y)$ are determined by the tube voltage and the tube current of the X-ray tube, thickness of the object, distance between the object and the detector, and grid conditions respectively.

As seen from equation (1), the intensity distribution of the scattered X-rays is given by a convolution integration of the function $f(Ip(x, y))$ of the primary X-ray intensity distribution and the function $g(x, y)$ of the impulse response. The experiment conducted by the inventors showed that a specific form of the equation (1), as given by the following equation (3), well described the intensity distribution of the scattered X-rays.

$$Isc(x, y) = A \int_{-a}^{a} \int_{-b}^{b} Ip^n(x', y')g(x - x', y - y')dy'dx' \quad (3)$$

Our study further showed that in equation (3), A, n and $g(x, y)$ depend on the tube voltage, the tube current, grid conditions, and the distance between the object and the detector, but scarcely depend on the thickness of the object. Of the above factors, n is selected between 0.5 and 1.5. The present invention is based largely on equation (3) defining the scattered X-ray intensity distribution.

Figure 3A:
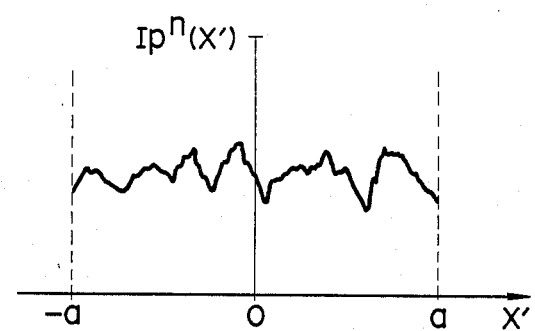
FIG. 3(A) graphically illustrates the spatial distribution of the primary X-rays' intensity.
Figure 3B:
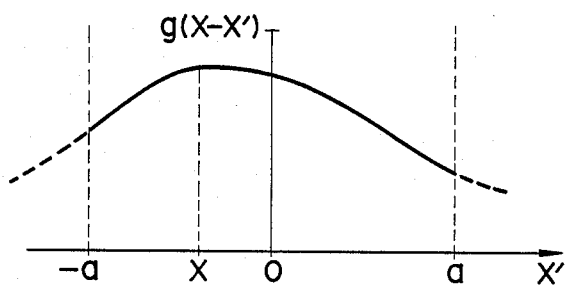
FIG. 3(B) graphically illustrates the impulse response function g(x) of the scattered X-rays.
Figure 3C:
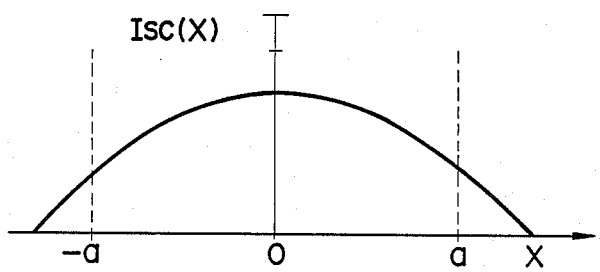
FIG. 3(C) illustrates the distribution of the scattered X-ray as the result of a convolution integration of the spatial distribution of the primary X-rays' intensity and the impulse response function g(x)

Equation (3) will further be discussed referring to FIG. 3. By convolution integrating the input signal $Ip^n(x')$ of the primary X-rays as shown in FIG. 3(A) and the function $g(x, y)$ slightly varying with respect to the positions as shown in FIG. 3(B), we have an intensity distribution (Isc(x) of the scattered X-rays as shown in FIG. 3(C). For purposes of simplicity of illustration, the functions in FIGS. 3(A) to 3(C) are depicted in a two-dimensional manner.

As seen from FIGS. 3(A) to 3(C), variation of the impulse response function $g(x, y)$ is more slight than the variation of the primary X-ray distribution $Ip(x, y)$ with respect to depositions. Based on this fact, equation (3) can approximately be rewritten into $$Isc(x, y) \simeq AIp^n \int_{-a}^{a} \int_{-b}^{b} g(x - x', y - y') dy' dx' \quad (4)$$

The total X-ray intensity distribution $Im(x, y)$ incident on the detector is the sum of the primary X-ray intensity distribution $Ip(x, y)$ and the scattered X-ray intensity distribution $Isc(x, y)$, and is given by $$Im(x, y) = Ip(x, y) + Isc(x, y) \quad (5)$$

and $$Ip(x, y) = Im(x, y) - Isc(x, y) \quad (5A)$$

The equation (5A) implies that if the intensity distribution of the scattered X-rays is known, the primary X-ray distribution can be obtained because the total X-ray distribution can easily be obtained by measuring the X-rays directly incident on the X-ray detector. Fortunately, the intensity distribution of the scattered X-rays component $Isc(x, y)$ is substantially equal over the entire projection area except at its peripheral edge. Therefore, an X-ray image formed by the primary X-rays can be obtained by subtracting the intensity of the scattered X-rays in a portion of substantially the center of the X-ray projection area, which is previously measured, from the transmitted X-ray image data derived from an object under examination. This is a first application principle of the invention.

If the impulse response function $g(x, y)$ can be expressed by a Gaussian function, it can be expressed as the following equation (2A)

$$g(x, y) = \frac{1}{2\pi\sigma_x\sigma_y} \exp(-x^2/2\sigma_x^2) \cdot \exp(-y^2/2\sigma_y^2) \quad (2A)$$

In the above equation, $\sigma_x$ and $\sigma_y$, like the factors A and n, depend on the grid condition and the distance between the object under examination and the X-ray detector, but little depends on the tube voltage of the X-ray tube and the thickness of the object under examination.

Therefore, equation (3) can be approximated to $$Isc(x, y) \simeq AIp^n \int_{-a}^{a} \int_{-b}^{b} g(x - x', y - y') dy' dx' \quad (4A)$$
$$= \frac{A}{2\pi\sigma_x\sigma_y} Ip^n \int_{-a}^{a} \int_{-b}^{b} \exp\{-(x - x')^2/2\sigma_x^2\} \times \exp\{-(y - y')^2/2\sigma_y^2\} dy' dx'$$
$$= C \int_{-a}^{a} \int_{-b}^{b} \exp\{-(x - x')^2/2\sigma_x^2\} \times \exp\{-(y - y')^2/2\sigma_y^2\} dy' dx'$$

where $C \equiv \frac{A}{2\pi\sigma_x\sigma_y} \overline{Ip}^n$

Also in this case, the above equation (5) holds, as a matter of course.

Therefore, if the factors C, $\sigma_x$ and $\sigma_y$ are known, $Isc(x, y)$ can be calculated using equation (4A) describing the intensity of the scattered X-rays. If $Isc(x, y)$ is obtained, $Ip(x, y)$ can be obtained by the equation (5A). Therefore, the scattered X-ray component is removed from an image composed of superposed images by primary X-rays and the scattered X-rays, using equation (4) describing the scattered X-ray model. This is a second application principle of the invention.

The following describes a method for obtaining the factors C, $\sigma_x$ and $\sigma_y$.

Figure 4:
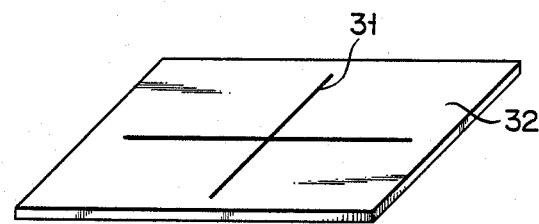
FIG. 4 is a perspective view of an acryl plate which is used as an X-ray shield plate in the system of the invention.
Figure 5:
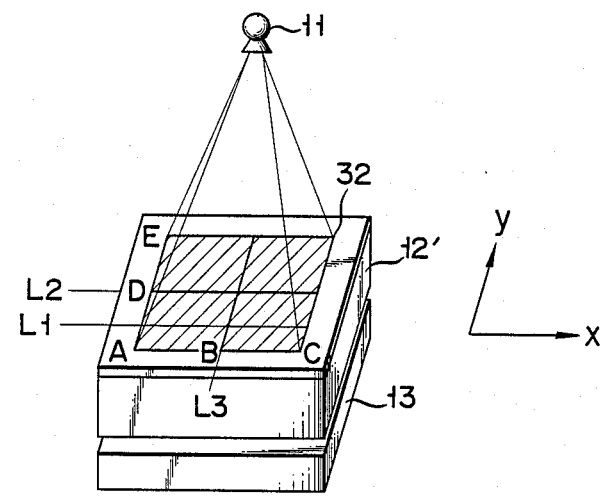
FIG. 5 is a diagram showing how the acryl plate is set at the time of X-ray irradiation.

For obtaining these factors, an X-ray shield plate is used which can shield the X-rays along the X-axis and Y-axis in the X-ray projection area. A thin plate 32, made of acryl resin, for example, and having a thin lead cross 31 thereon, as shown in FIG. 4, may be used for the X-ray shield plate. As shown in FIG. 5 the, acryl plate 32 is placed on a phantom 12', with an X-ray tube 11 located above the acryl plate 32. An X-ray detector 13 is further disposed just under the phantom 12'. In operation, X-rays are radiated by the X-ray tube, transmitted through the acryl plate 32 and the phantom 12', and detected by the detector 13. The intensity of the transmitted X-rays differs with locations on the acryl plate 32 bearing the lead cross 31, which is irradiated with X-rays. For example, along a line L1 on the acryl plate 32 in FIG. 5, the X-ray intensity is distributed as shown in FIG. 6(A). The X-ray intensity along lines L2 and L3 on the acryl plate 32 are as shown in FIGS. 6(B) and 6(C). The X-ray intensities shown in FIGS. 6(B) and 6(C) are those of only the scattered X-rays since the primary X-rays are shielded by the lead 31 on acryl plate 32. Using the equation (4A), we can express the X-ray intensity along the line L2 as follows $$Isc(x, o) = C \int_{-b}^{b} \exp(-y'^2/2\sigma_x^2) dy' \times \int_{-a}^{a} \exp\{-(x - x')^2/2\sigma_x^2\} dx' \quad (6)$$
$$= C \cdot C1 \cdot F1(x)$$

where $$C1 = \int_{-b}^{b} \exp(-y'^2/2\sigma_y^2) dy' \quad (7)$$

$$F1(x) = \int_{-a}^{a} \exp\{-(x - x')^2/2\sigma_x^2\}dx' \quad (8)$$

In the above equations, C and C1 are constants and F1(x) is a function describing the x-dependency of the scattered X-rays. In a similar way, the X-ray intensity distribution along the line L3 can be expressed $$Isc(o, y) = C \cdot C2 \cdot F2(y) \quad (9)$$

where $$C2 = \int_{-a}^{a} \exp(-x'^2/2\sigma_x^2)dx' \quad (10)$$

$$F2(y) = \int_{-b}^{b} \exp\{-(y - y')^2/2\sigma_y^2\}dy' \quad (11)$$

In these expressions, C and C2 are constants, and F2(y) is a function describing the y-dependency of the scattered X-rays distribution.

By applying a fitting process to the X-ray intensity distribution curve of the X-rays detected on the line L2, values for C×C1 and F1(x) most closely approximating the intensity distribution curve, can be obtained. C1 and C2 can respectively be obtained by using the equations (7) and (10) since $\sigma_x$ and $\sigma_y$ can be obtained by F1(x) and F2(y) already obtained.

In this way, values for C, $\sigma_x$ and $\sigma_y$ are obtained.

In the embodying the present invention based on the second application principle, to find the scattered X-ray intensity distribution, both the x- and y-dependencies are not necessarily obtained, and it is satisfactory to obtain either of them if necessary.

A first embodiment of an X-ray diagnostic apparatus according to the present invention, which is based on the first principle, will be described referring to FIGS. 7 and 10.

In FIG. 7, there is shown an illustrative X-ray diagnostic apparatus as a first embodiment of the present invention, and is designed on the first application principle.

In the figure, reference numeral 45 designates an X-ray generator such as an X-ray tube. An X-ray shield plate 47 is located within an X-ray projection area and between object 46 under examination and the X-ray tube 45. The X-ray shield plate 47 will be described in detail later. An X-ray detector 48 detects X-rays transmitted through the object 46. An A/D converter 49 converts to digital data analog signals output from the X-ray detector 48. First and second switching circuit means 52 and 53 are provided between the A/D converter 49 and a memory 50. Fixed contacts B and B of these switches have a substractor 51 connected therebetween which is additionally connected to a scattered X-ray intensity-computing circuit means 54 for receiving data from the memory 50.

The switching circuit means 52 and 53 are connected with a controller 55. These switching means cooperate to form a path between the A/D converter and the memory 50 when the object 46 is irradiated under a condition in which the X-ray shield plate 47 is placed in the X-ray projection area. Those switches form another path containing the subtracting circuit means 51 between the A/D converter 49 and the memory 50 when the object is irradiated under a condition in which the X-ray shield plate 47 is placed outside the X-ray projection area. The memory 50 is for storing the detected image data output from the A/D converter 49 through the respective paths. A circuit means 54 computes the intensity of the scattered X-rays while using the detected image data fetched from the memory 50. The subtracting circuit means 51 subtracts the computed scattered X-ray intensities from the data collected under the condition that the object 46 is irradiated after removal of the X-ray shield plate 47 from the X-ray projection area. The controller 5 controls the timing of the operation of the first and second switching circuit means 52 and 53, and the X-ray shield plate 47. A monitor 56, coupled with the output of the memory 50, visualizes for monitoring the image data of only the primary X-rays stored in the memory 50. An X-ray aperture 57, defining the X-ray projection area, is disposed close to the X-ray tube 25.

A drive means (not shown) under control by the controller 55 drives the X-ray shield plate 47 to place it in and retract it from the X-ray projection area. The X-ray shield plate 47 is formed of a thin plate 47B made of acryl resin, for example, which has an X-ray shield member, such as a lead piece 47A, located at the center of the X-ray projection area, as shown in FIG. 8. The object 46 is irradiated by the X-ray tube 45 while the X-ray shield plate 47 is placed in the X-ray projection area, as shown in FIG. 9. In this test, the intensity distribution of the X-rays detected by the X-ray detector 48 along a line A—A' in FIG. 9 is plotted as shown in FIG. 10. It is seen from FIG. 10 that the distribution curve is substantially flat over the X-ray projection area, while having a local minimum point at the center of the X-ray projection area. The intensity of the scattered X-rays Isc at the minimum point is due to the scattered X-rays Isc and has substantially equal values over the entire X-ray projection area.

The scattered X-ray intensity computing circuit means 54 averages the detected image data of picture elements in an area of the X-ray shield plate 47 covered by the lead piece 47A, and provides the averaged value as the scattered X-rays component input.

The operation of the X-ray diagnostic apparatus thus arranged on the basis of the first principle will be described below.

For obtaining the intensity of the scatttered X-rays, the X-ray shield plate 47 is placed in the X-ray projection area. Then, the switching circuit means 52 and 53 are set to the fixed contacts A and A to form a path directly connecting the A/D converter 49 to the memory 50. Then, the X-ray tube 45, is driven to irradiate the object 46 while the X-ray shield plate 47 is placed in the X-ray projection area. The X-ray detector 48 detects the X-rays transmitted through the object 46 to produce analog output-image data. The image data generated by the portion of detector 48 in line with lead piece 47A of shield plate 47 contains only the scattered X-rays. The image data is A/D converted by the A/D converter connected at the succeeding stage. The converted image data is stored in a first section of the memory 50 through the path A—A formed by the switching circuit means 52 and 53. The memory applies the image data of the picture elements corresponding to lead-piece covering portion on the X-ray shield plate 47 to the scattered X-ray intensity-computing circuit means 54. This circuit means 54 averages the stored data over the number of picture elements corresponding to shield section 47A, stored in the first section of memory 50, and produces it as the scattered X-ray component data. The averaging of such data is performed for reducing contained noise.

In the next step, the X-ray shield plate 47 is retracted from the X-ray projection area. Then, the switching circuit means 52 and 53 are operated such that the output of the A/D converter 49 is connected through the subtraction circuit 51 to the memory 50. Succeedingly, the X-ray tube projects X-rays into the object 46, while the X-ray shield plate 47 is put outside the X-ray projection area. The X-ray detector 48 detects the X-rays transmitted through the object 46. The image data collected here contains both the primary X-rays and the scattered X-rays. The A/D converter 49 converts to digital data the image (analog) data output from the X-ray detector 48 and applies the digital data to the subtracting circuit means 51 through the first switch B. The subtracting circuit means 51 subtracts from the image (digital) data thus obtained the detected data as the scattered X-ray component, which comes from the first section of memory 50 via the averaging means 54. Thus obtained image data of only the primary X-rays is applied to a second section of the memory 50 and then to the monitor 56. In this way, the monitor 56 displays the X-ray image based on only the primary X-rays.

As described above, in the embodiment of FIG. 7, in the first step for obtaining the scattered X-rays component, X-rays are projected into the object 46 under examination under the condition that the X-ray shield plate 47 is placed in the X-ray projection area on the X-ray incident side of the object 46. In the second step for obtaining the image data containing both the primary X-rays component and the scattered X-rays component, the X-ray shield plate is retracted from the X-ray projection area, and the object 46 is irradiated with X-rays radiated from the X-ray tube 45. In the third step, the scattered X-rays component is subtracted from the image data in the second step, thereby to obtain the image data containing only the primary X-rays. Using such image data, an X-ray image of the object is displayed by the monitor. Therefore, the displayed X-ray image is free from blur and good in contrast and sharpness.

The above-mentioned embodiment may be modified into an arrangement as shown in FIG. 11 in which a logarithm-converting circuit means 58 is additionally provided following the subtracting circuit means 51. The logarithm-converting circuit means 58 converts the output signal Ip(x, y) from the subtracting circuit means 51 into a natural logarithmic value. The provision of the logarithm-converting processing circuit means enables one to obtain an attenuation quantity of X-rays $$\left( \sum_i \mu_i d_i \right)$$

in the following way. The X-ray intensity Ip(x, y) of only the primary X-rays can be expressed by $$Ip(x, y) = Ioe^{-\sum_i \mu_i(x, y) d_i(x, y)} \quad (12)$$

In the above equation, Io is the intensity of X-rays incident on the X-ray detector 48, which depends on the conditions which the X-ray tube has when there is no object. And $\mu_i(x, y)$ is an X-ray absorbing coefficient of tissues (i) of the object 46. Further $d_i(x, y)$ describes the thickness of the object 46 as a function of x and y, which define the position on the tissue (i) of the object 46 corresponding to a position on the X-ray detector 48 hit with an X-ray beam. If the exponential expression (12) is expressed in the form of the natural logarithm, we have the following logarithmic expression (13).

$$\ln Ip(x, y) = \ln Io - \sum_i \mu_i(x, y) d_i(x, y) \quad (13)$$

In the above equation, ln Io is a known value. Therefore, the attenuation quantity of the X-rays $$\left( \sum_i \mu_i(x, y) d_i(x, y) \right)$$

can be obtained using the equation (13).

As seen from the foregoing description, by subtracting the scattered X-ray component as previously defined from the X-rays transmitted through the object, a formed transmitted X-ray image depends solely on the primary X-rays. Therefore, the following useful effects can be attained:

(1) to improve contrast and resolution of the image of the patient.

(2) to exactly obtain an X-ray attenuation quantity by logarithmically converting the image data.

The effect (2) above is more effective particularly for the X-ray diagnosis carried out using an X-ray constrast medium. Specifically, in handling a subtraction image between the images before and after the contrast medium is administered, if the subtraction is performed after both of these images are logarithmically converted, it is possible to exactly obtain the product $\Delta\mu \cdot d$ of a changed amount of $\Delta\mu$ of an X-ray coefficient, which is caused by the contrast medium and the thickness "d" of the tissue under X-ray radiation.

Figure 12:
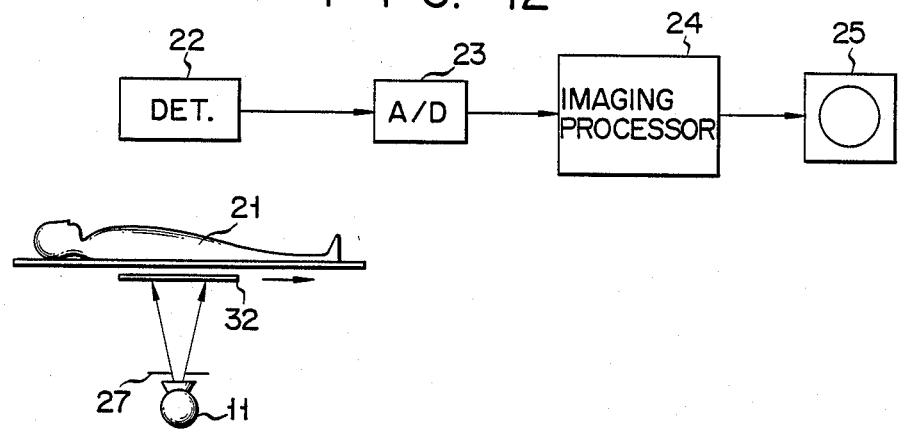
FIG. 12 is a schematic diagram showing of another embodiment of an X-ray diagnostic apparatus according to the present invention.

A second embodiment of an X-ray diagnostic apparatus according to the present invention, which is based on the second application principle, will be described referring to FIG. 12. In the figure, X-rays radiated from an X-ray generator 11 transmit through the acryl plate 32 and the object 21 under examination, and enter into an X-ray detector 22. The X-ray detector 22 detects the intensity of the transmitted X-rays. An A/D converter is used for converting to digital signal and the analog image signals output by the X-ray detector 22. An image processor 24 includes a memory for storing image data, and a computing means for removing the scattered X-ray component from the image data, as will subsequently be described. Reference numeral 25 designates a monitor for displaying the image data processed by the image processor 24.

The acryl plate 32 has a structure as shown in FIG. 4. For X-ray irradiation to determine the scattered X-rays intensity or to obtain the parameters C, $\sigma_x$ and $\sigma_y$, the acryl plate 32 is placed in the X-ray projection area. After these parameters are determined, it is retracted from the X-ray projection area. The movement of the acryl plate 32 is made by a drive means (not shown).

The image processor 24 contains a scattered X-ray intensity computing section 24A and a compensating section 24B.

Figure 13:
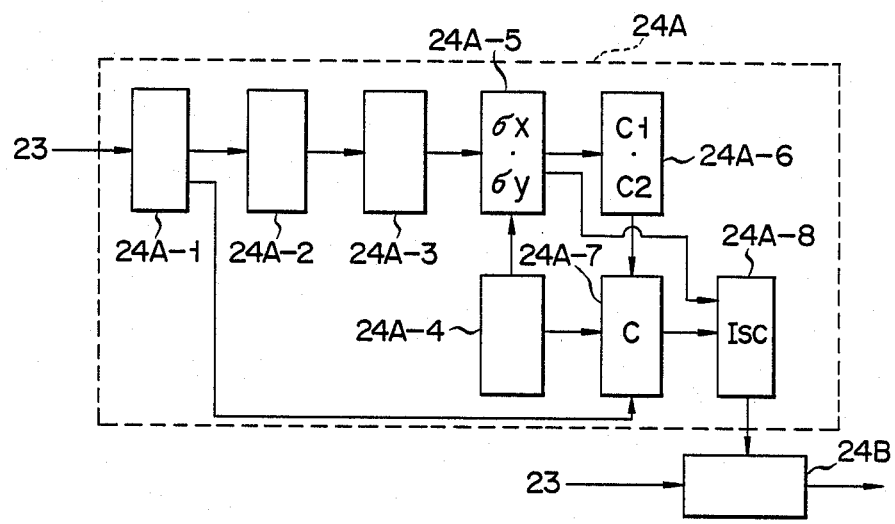
FIG. 13 shows in block diagram form an image processor used in the embodiment of FIG. 12.

In FIG. 13 illustrating the image processor, a first memory 24A-1 temporarily stores, of the detected signals output from the X-ray detector 22, a detected signal $Isc^{ob}(0, 0)$ representing X-ray intensity at positions (x, 0) and (0, y) on the lines L2 and L3 on the acryl plate 32. A computing means, for example, a low-pass filtering means 24A-2, cuts off the high frequency component in the detected signal. A normalizing means 24A-3 noramlizes the detected signals Isc(x, 0) and Isc(0, y) after the high frequency component is cut off by a detected signal Isc(0, 0) representing an X-ray intensity at a center position (a cross point of the lines L2 and L3). A second memory 24A-4 stores functions $F1^{cal}(x)$ and $F2^{cal}(y)$ previously calculated for various parameters $\sigma_x$ and $\sigma_y$, and the normalized functions $Fa^{cal}(x)/F1^{cal}(0)$ and $F2^{cal}(y)/F2^{cal}(0)$. A $\sigma$ parameter determining means 24A-5 compares $F1^{ob}(x)/F1^{ob}(0)$ and $F2^{ob}(x)/F2^{ob}(0)$ output from the normalizing means 24A-3, $F1^{cal}(x)/F1^{cal}(0)$ $F2^{cal}(y)/F2^{cal}(0)$ output from the second memory 24A-4, and determines parameters $\hat{\sigma}_x$ and $\hat{\sigma}_y$ to provide the most approximate $F1^{cal}(x)/F1^{cal}(0)$ and $F2^{cal}(y)/F2^{cal}(0)$. A C1, C2 determining means 24A-6 determines C1 and C2 by the equations (7) and (10), using the parameters $\hat{\sigma}_x$ and $\hat{\sigma}_y$. A C determining means 24A-7 determines $\hat{C}$ by the equation (6), using the parameters C1 and C2 and the detected signal $Isc^{ob}(0, 0)$ stored in the first memory 24A-1. A scattered X-ray intensity-computing means 24A-8 computes the scattered X-ray intensity Isc(x, y) at a proper position by the equation 4A, using the parameters $\hat{\sigma}_x$, $\hat{\sigma}_y$ and C, and stores the computed one. The compensating means 24B contains a subtractor for subtracting, by the equation (5A), a signal Isc(x, y) representing the scattered X-ray intensity, obtained by the scattered X-ray intensity-computing means 24A-8, from a detected signal Im(x, y), produced from the X-ray detector 22, when the X-rays transmitted through the object 21 are detected by the X-ray detector with retraction of the acryl plate 32 from the X-ray projection area. An X-ray aperture 27 (FIG. 12), defining the X-ray projection area, is disposed close to the X-ray generator 11.

The operation of the X-ray diagnostic apparatus thus arranged will be described.

Figure 14A:
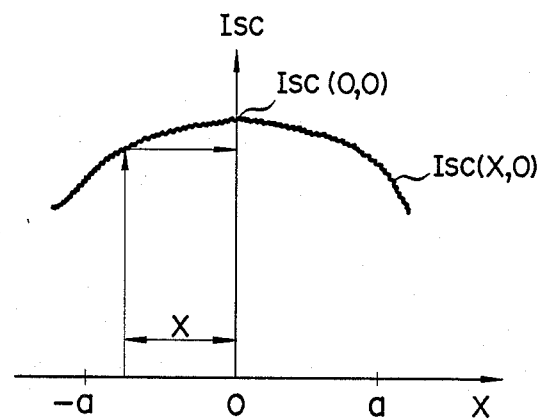
FIG. 14 are graphs showing the determination of parameters $\sigma_x$, $\sigma_y$ and C employed in the second embodiment, wherein FIG. 14(A) graphically illustrates the intensity distribution of the scattered X-rays detected in the X direction.
FIG. 14(B) illustrates the intensity distribution curve of X-rays with a high frequency component cut off, the curve being normalized at the center position.
FIG. 14(C) illustrates a normalized curve describing $F1^{cal}(x)$ with the parameter of $\sigma_x$.
Figure 14B:
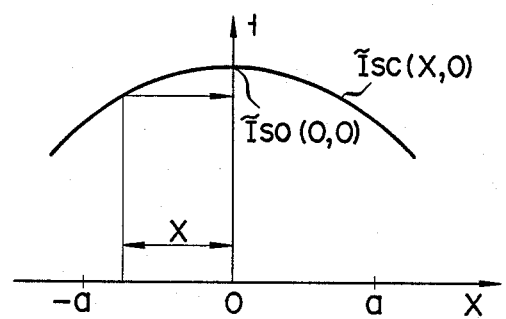
Figure 14C:
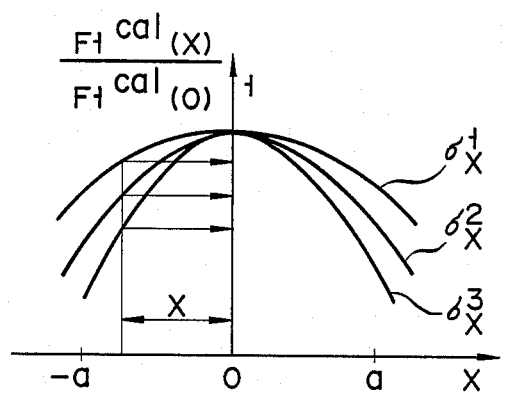

To obtain the scattered X-ray intensity, the acryl plate 32 is set in the X-ray projection area and the X-ray tube projects X-rays into the object 21. The X-rays transmitted through the object 21 are detected by the X-ray detector 22. A detected signal from the X-ray detector 22 is converted to digital data by the A/D converter 23 and is supplied to the image processor 24. Of those detected signals supplied to the image processor 24, the detected signals Isc(x, 0) and Isc(0, y) of the X-rays on the lines L2 and L3 on the acryl plate 32 are stored in the first memory 24A-1. As shown in FIG. 14(A), the detected signal Isc(x, 0) contains high frequency noise. The detected signal is passed through the low-pass filtering means 24A-2 where its high frequency component is cut off. The detected signal $\overline{Isc}(x, o)$, after passing the low-pass filter, is as shown in FIG. 14(B). Then, the detected signal $\overline{Isc}(x, 0)$ and the detected signal $\overline{Isc}(0, 0)$ at the center position are applied to the normalizing means 24A-3 where the detected signal $\overline{Isc}(x, 0)$ is normalized by the detected signal $\overline{Isc}(0, 0)$. Here, the normalizing means performs the operation of $\overline{Isc}(x, 0)/\overline{Isc}(0, 0)$. The result of the normalizing represents $F1^{ob}(x)/F1^{ob}(0)$ according to the equation (6). The second memory 24A-4 stores $F1^{cal}(x)/F1^{cal}(0)$ (see FIG. 14C) and F1(x) is normalized by $F1^{cal}(x)$ and $F1^{cal}(0)$ obtaining by using various values of $\sigma_x$ according to the equation (8). The $\sigma$ determining means 24A-5 compares $F1^{ob}(x)/F1^{ob}(0)$ output from the normalizing means 24A-3 and the various normalized functions $F1^{cal}(x)/F1^{cal}(0)$ output from the second memory 24A-4, and determines $\sigma_x$ to provide the most approximate $F1^{cal}(x)/F1^{cal}(0)$. The $\hat{\sigma}_x$ determined by the $\hat{\sigma}$ determining means 24A-5 is output to the C1/C2 determining means 24A-6. This means 24A-6 performs the operation of the equation (10) to determine C2 using $\hat{\sigma}_x$, and sends the determined C2 to the C determining means 24A-7. The C determines means 24A-7 determines $\hat{C}$ by the equation (6) using the value of C2, the function $F1^{cal}(0)$ stored in the second memory 24A-4, and the actually measured data $Isc^{ob}(0, 0)$ stored in the first memory 24A-1, and sends the C to the scattered X-ray intensity-computing means 24A-8. Similarly, $\sigma_y$ is determined by the detected signal Isc(0, y). The scattered X-ray intensity-computing means 24A-8 performs the operation of the equation (4A), using thus determined $\hat{\sigma}_x$, $\hat{\sigma}_y$ and $\hat{C}$ to obtain a signal Isc(x, y) representing a scattered X-ray intensity at a proper position and stores this signal.

Following the computing of the scattered X-ray intensity, the acryl plate 32 is retracted from the X-ray projection area, and then the object 21 is irradiated with X-rays. The X-rays transmitted through the object 21 are detected by the X-ray detector 22. A signal output from the X-ray detector 22 is then applied to the A/D converter 23 where it is converted to digital data. The converted digital data is applied, as the output signal Im(x, y), to the compensating processing section 24B in the image processor 24. In the compensating section 24B, the equation (5A) is performed to have the image signal Ip(x, y) containing only the primary X-ray component.

In this way, the scattered X-ray component is removed from the transmitted X-ray data containing both the primary X-ray component and the scattered X-ray component, and the X-ray image based only on the primary X-ray component is visually displayed by the monitor.

Figure 15:
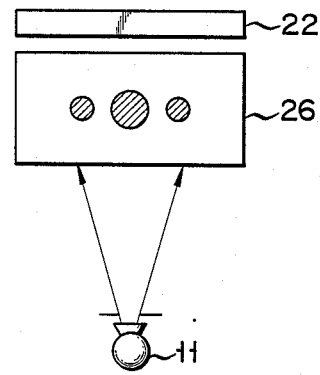
FIG. 15 is a diagram illustrating use of a contrast phantom in connection with the second embodiment.

When a contrast phantom 26 is radiographed by using the x-ray diagnostic apparatus thus arranged, as shown in FIG. 15, the X-ray detector 22 produces a detected signal Im(x, y) containing the scattered X-ray component, as shown in FIG. 16(A). A signal Isc(x, y) representing a scattered X-ray intensity distributed as shown in FIG. 16(B), which is produced from the scattered X-ray intensity-computing section 24A, is subtracted from the detected signal Im(x, y). Through this subtraction, a signal Ip(x, y) containing only the primary X-rays can be obtained as shown in FIG. 16(C). Therefore, the X-ray image displayed by the monitor 25 is improved in contrast and sharpness, and is free from blur.

Although not shown, the image processor 24 contains a controller containing a CPU for providing control signals to extract the detected signals Isc(x, 0) and Isc(0, y) of the X-rays along the lines L2 and L3 and stores them in the related memory, and various control signals necessary for operating the scattered X-ray intensity-computing section 24A and the compensating processing section 24B.

Having described specific embodiments, it is believed obvious that modification and variation of our invention are possible in light of the above teachings.

For example, the scattered X-ray intensity-computing section 24A in the image processing unit 24 in the second embodiment may be replaced by a means in which $\sigma$ is determined by the least square method. For the function g(x, y), an exponential function corresponding relatively well to the results of experiment may be used in place of the Gauss function.

What is claimed is:

1. An X-ray diagnostic apparatus of the type in which trasmitted X-ray image data, produced by an X-ray detector as the result of irradiating an object in an X-ray projection area, is digitized and visually displayed, said apparatus comprising:

X-ray shield means having an X-ray shield section consisting essentially of a pair of X-ray blocking, orthogonally interseccting straight lines forming X and Y axes;

means for moving said shield means into and out of the path of said X-rays irradiating said object, said X-ray shield section, when in said X-ray path, causing the generation of X-ray transmission image data containing X and Y axis shield data;

means for computing a scattered X-ray component signal using said X and Y axis shield data in accordance with a mathematical algorithm describing scattered X-ray intensity for an object like a human body based on an impulse response function having a Gaussian form; and compensating means for subtracting said scattered x-ray component signal from the transmitted X-ray image data produced when said X-ray shield means is retracted from said X-ray path, thereby producing image data comprising a primary X-ray component and a minimized scattered X-ray component.

2. The apparatus according to claim 1, in which said means for computing includes first memory means for temporarily storing the transmitting X-ray transmission image data containing said X and Y axis shield data for at least one of the X and Y axes, normalizing means for normalizing the transmitted X-ray image data based on the X-ray intensity at a reference position on said X-ray shield section, second memory means for storing predetermined function data for computing said scattered X-ray component signal and normalized data of said function data, and scattered X-ray intensity computing and storing means for computing the values of the parameters of said impulse response function based on the data stored in said first and second memory means and for storing scattered X-ray intensity values for predetermined positions in said X-ray shield section.

3. The apparatus according to claim 1, in which said X-ray shield section is an acrylic plate having a lead mask configured to form said intersecting straight lines.

4. The apparatus according to claim 3, in which said acrylic plate constituting said X-ray shield section is selectively placed on a phantom.

5. The apparatus according to claim 2, in which said reference position data used to effect the normalization in said normalizing means is taken from the center position on said X-ray shield section.

6. The apparatus according to claim 2, in which said scattered X-ray intensity computing means further includes high frequency suppressing means for suppressing the high frequency component in said transmitted X-ray image data containing said X and Y axis shield data.

7. The apparatus according to claim 6, in which said high frequency suppressing means comprises a low-pass filter.

* * * * *